United States Patent [19]

Acker et al.

[11] 4,363,925

[45] Dec. 14, 1982

[54] PREPARATION OF AROMATIC SILANES

[75] Inventors: Rolf-Dieter Acker, Leimen; Gerhard Hamprecht, Weinheim; Franz-Josef Mueller, Wachenheim, all of Fed. Rep. of Germany

[73] Assignee: BASF Aktiengesellschaft, Fed. Rep. of Germany

[21] Appl. No.: 339,503

[22] Filed: Jan. 15, 1982

[51] Int. Cl.$^3$ .............................. C07F 7/08; C07F 7/10; C07F 7/18

[52] U.S. Cl. .................................. 556/415; 556/416; 556/417; 556/422; 556/418; 556/420; 556/438; 556/437; 556/445; 556/468

[58] Field of Search ............... 556/415, 416, 417, 422, 556/418, 420, 438, 437, 445, 468

[56] References Cited

U.S. PATENT DOCUMENTS 3,772,347  11/1973  Atwell et al. ..................... 556/468
3,878,234   4/1975  Atwell et al. ..................... 556/468
4,059,607  11/1977  Reedy et al. ...................... 556/468

Primary Examiner—Paul F. Shaver
Attorney, Agent, or Firm—Keil & Witherspoon

[57] ABSTRACT

Aromatic silanes are prepared by reacting an aromatic halogen compound with a disilane in the presence of a palladium complex and a phosphite or phosphine.

The aromatic silanes obtainable by the process of the invention are valuable intermediates for the preparation of drugs, dyes and pesticides.

9 Claims, No Drawings

PREPARATION OF AROMATIC SILANES

The invention relates to a novel process for the preparation of aromatic silanes by reacting an aromatic halogen compound with a disilane in the presence of a palladium complex and a phosphite or phosphine.

The reaction of a haloaromatic compound with an alkali metal, particularly lithium or sodium, and a chlorosilane, and the reaction of a haloaromatic compound with magnesium and a chlorosilane in a Grignard-type reaction (Synthesis (Review) 11 (1979), 841–876) are known processes for the preparation of aromatic silicon compounds. The cleavage of hexamethyldisilane with potassium t-butylate and subsequent substitution of the haloaromatic compound by the trimethylsilyl radical also leads to silylaromatic compounds. All of these processes have the disadvantage of requiring extreme basic reaction conditions, and giving unsatisfactory yields in some cases. In most cases it is not possible to use this reaction in the presence of base-sensitive functional substituents of aromatics, eg. nitro, cyano or carboxylate substituents.

Furthermore, it is known that nitrohalobenzenes give nitrophenyltrimethylsilanes when from 1.8 to 2.5 equivalents of hexamethyldisilane per equivalent of nitrohalogenoaromatic are employed, with tetrakis-(triphenylphosphine)-palladium as the catalyst (H. Matsumoto, K. Yoshihiro, S. Naghashima, H. Watanabe and Y. Nagai, J. Organomet. Chem. 128 (1977), 409–413). In this process, in order to achieve good yields, the reaction mixture mixed under inert gas in a glass tube is cooled with liquid nitrogen, and the glass tube is evacuated, sealed and then heated to 150° in the course of 40 hours. The tetrakis(triphenylphosphine)-palladium required as the catalyst is obtainable in pure form only with considerable preparative expense and is very sensitive to oxidation when in solution (see Inorganic Synthesis, Vol. XIII, pages 121–123).

We have found that aromatic silanes of the formula:

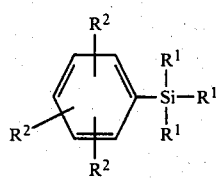

where the individual radicals $R^1$ and $R^2$ can be identical or different and each is an aliphatic cycloaliphatic, araliphatic or aromatic radical, and each radical $R^2$ can also be hydrogen, halogen, nitro, cyano, —O—$R^3$,

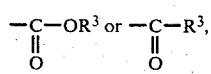

where $R^3$ is an aliphatic, cycloaliphatic, araliphatic or aromatic radical, are advantageously obtained when an aromatic halogen compound of the formula:

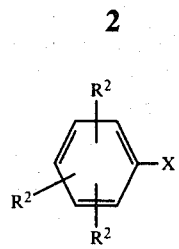

where $R^2$ has the above meaning and X is halogen, is reacted with a disilane of the formula:

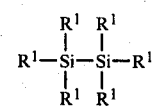

where $R^1$ has the above meaning, in the presence of a palladium complex with a ketone and/or an anhydride, and in the presence of a phosphine or phosphite which is trisubstituted by aliphatic or aromatic radicals.

Where methyl 4-chlorobenzoate and hexamethyldisilane are used, the reaction can be represented by the following equation:

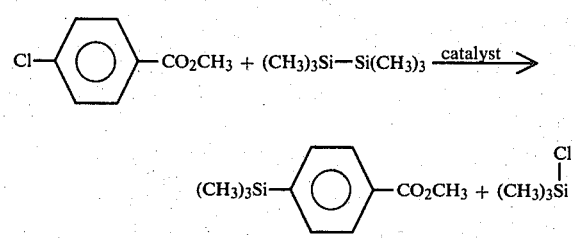

Compared to the conventional processes, the process according to the invention gives aromatic silanes by a simpler and more economical route and in better yield and purity. All of these advantageous results are surprising in view of the prior art.

The disilanes III can readily be prepared, for example according to the process described in J. Organometal. Chem., 13 (1968), 323–328. They can be reacted in stoichiometric amounts or in an excess, preferably in an amount of from 0.5 to 2.0, in particular from 1.0 to 1.3, moles of starting material III per mole of starting material II. Preferred starting materials II and III and, accordingly, preferred end products I are those in whose formulae the individual radicals $R^1$ and $R^2$ can be identical or different and each is alkyl of 1 to 7 carbon atoms, cycloalkyl of 5 to 8 carbon atoms, aralkyl of 7 to 12 carbon atoms or phenyl which is unsubstituted or is monosubstituted or disubstituted by chlorine, bromine, alkyl or alkoxy, each of 1 to 4 carbon atoms, nitro and/or cyano, and each radical $R^2$ can also be hydrogen, fluorine, bromine, chlorine, nitro, cyano, —O—$R^3$,

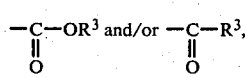

where $R^3$ is alkyl of 1 to 4 carbon atoms, cycloalkyl of 5 to 8 carbon atoms, aralkyl or alkylaryl, each of 7 to 12 carbon atoms, or phenyl which is unsubstituted or is monosubstituted or disubstituted by chlorine, bromine, alkyl or alkoxy of 1 to 4 carbon atoms each, nitro and/or cyano, and X is bromine or, in particular, chlorine.

The above radicals can additionally be substituted by groups which are inert under the reaction conditions, for example alkyl or alkoxy, each of 1 to 4 carbon atoms.

Examples of suitable starting materials II are chlorobenzene, bromobenzene, chlorobenzenes which are monosubstituted in the 2-, 3- or 4-position or identically or differently disubstituted in the 2,3- 2,4-, 2,5-, 2,6-, 3,5- or 3,4-position or identically or differently trisubstituted in the 2,3,4-, 2,4,6-, 3,4,5-, 2,4,5- or 2,5,6-position by chlorine, bromine, nitro, cyano, methyl, ethyl, propyl, isopropyl, butyl, sec.-butyl, isobutyl, tert.-butyl, methoxy, ethoxy, propoxy, isopropoxy, butoxy, isobutoxy, sec.-butoxy, tert.-butoxy, methylcarboxy, ethylcarboxy, propylcarboxy, isopropylcarboxy, butylcarboxy, isobutylcarboxy, sec.-butylcarboxy, tert.-butylcarboxy, methylcarbonyl, ethylcarbonyl, propylcarbonyl, isopropylcarbonyl, butylcarbonyl, isobutylcarbonyl, sec.-butylcarbonyl, tert.-butylcarbonyl, benzylcarbonyl, cyclohexylcarbonyl, phenylcarbonyl, benzoxy, cyclohexoxy, phenoxy, benzylcarboxy, cyclohexylcarboxy or phenylcarboxy, and similarly substituted bromobenzenes.

Examples of suitable starting materials III are hexamethyldisilane, hexaethyldisilane, hexapropyldisilane, hexaisopropyldisilane, hexabutyldisilane, hexa-sec.-butyldisilane, hexaisobutyldisilane, hexa-tert.-butyldisilane, tetramethyldimethyldisilane, hexabenzyldisilane, hexacyclohexyldisilane and hexaphenyldisilane.

As a rule, the reaction is carried out at from 50° to 250° C., advantageously from 100° to 200° C., in particular from 130° to 180° C., under atmospheric pressure or superatmospheric pressure, continuously or batchwise. Solvents which are inert under the reaction conditions are advantageously used, examples of suitable solvents being aromatic hydrocarbons, eg. toluene, ethylbenzene, o-xylene, m-xylene, p-xylene, isopropylbenzene and methylnaphthalene, ethers, eg. ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran and dioxane, esters, eg. methyl acetate, n-propyl acetate, methyl propionate, butyl acetate, ethyl formate, methyl phthalate, methyl benzoate, ethyl acetate and phenyl acetate, nitriles, eg. acetonitrile, butyronitrile, isobutyronitrile, benzonitrile and m-chlorobenzonitrile, dimethylformamide, diethylformamide, dimethylacetamide, diethylacetamide, N-methylpyrrolidone, sulfolane and hexamethylphosphorotriamide, aliphatic or cycloaliphatic hydrocarbons, eg. heptane, α-pinene, pinane, nonane, gasoline fractions of boiling ranges from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, and ketones, eg. dialkyl ketones and aryl alkyl ketones, and mixtures of the above. The solvent is advantageously used in an amount of from 100 to 10,000 percent by weight, preferably from 200 to 1,000 percent by weight, based on starting material II.

As a rule, the ketone or anhydride used has 2 or more carbonyl groups, triple bonds and/or double bonds. Examples of suitable anhydrides are fumaric anhydride, cinnamic anhydride, acrylic anhydride, oleic anhydride, propargylic anhydride, acetoacetic anhydride, allylacetic anhydride, vinylacetic anhydride and, preferably, maleic anhydride. Examples of suitable ketones are acetyl-acetone, bis-acetyl-acetone, acetonedicarboxylic acid anhydride, acetone dioxalates, acetonylacetone, acetyl-benzoyl, acetyl-pyruvic acid, benzalacetone and dibenzalacetone, the latter being preferred. In general, from 0.001 to 0.2, in particular from 0.01 to 0.1, gram of palladium is used per mole of starting material II and from 0.5 to 5.0, in particular from 1.5 to 4.5, moles of ketone or anhydride ligand are used per gram atom of palladium.

An additional catalyst is also used, this being a trisubstituted phosphine or phosphite, in general, of the formula:

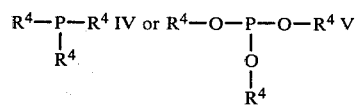

where the individual radicals $R^4$ can be identical or different and each is an aliphatic radical, preferably alkyl of 1 to 6 carbon atoms, or an aromatic radical, preferably phenyl which is unsubstituted or is substituted by alkyl or alkoxy of 1 to 4 carbon atoms each, bromine, chlorine, nitro or cyano. Examples of suitable compounds IV and V are trimethylphosphine, triethylphosphine, tripropylphosphine, triisopropylphosphine, tributylphosphine, triisobutylphosphine, tri-sec.-butylphosphine, tri-tert.-butylphosphine and triphenylphosphine, and homologously substituted phosphites. In general, the additional catalyst is used in an amount of from 0.0001 to 0.8, in particular from 0.001 to 0.4, mole of phosphine or phosphite per mole of starting material II.

The reaction can be carried out as follows: a mixture of the starting materials II and III, the compound IV or V and the palladium complex is kept at the reaction temperature for from 40 to 60 hours. It is not absolutely necessary to carry out the reaction under a protective gas, but the use of nitrogen or argon is advantageous when palladium ligands which are sensitive to oxidation are employed. The temperature and the reaction time in the novel process depend on the nature of the substituents and the aromatics. The process is advantageously carried out as follows: The palladium complex is introduced into the solvent and the compound IV or V is then added. The starting materials II and III are introduced and the mixture is then heated in a closed system to 100°-200° C., preferably 130°-180° C. The sequence of addition of the compounds of the formulae II, III, IV and V and the complex, and the pressure used, are not critical. The end product is separated off in a conventional manner, for example by adding hydrocarbons to precipitate the catalyst and separating off the latter, and is isolated and purified by distillation, recrystallization or chromatography, after evaporating down the solvent. Features to be emphasized are that the non-sensitive silylation catalyst is prepared in the reaction mixture, thereby avoiding expensive isolation steps, and that only a small excess of the disilane of the formula III is necessary.

The aromatic silanes obtainable by the process of the invention are valuable intermediates for the preparation of drugs, dyes and pesticides. Regarding their use, reference may be made to the above publications and to German Laid-Open Application DOS No. 2,507,929 or European Patent Application No. 6,184.

In the examples which follow, parts are by weight.

EXAMPLE 1

1.05 parts of triphenylphosphine are added to a mixture of 9.84 parts of 2-chloronitrobenzene in 35 parts of xylene and 1.15 parts of dibenzalacetone-palladium. After stirring at 22° C. for 30 minutes, 11 parts of hexamethyldisilane are added and the mixture is heated in a stirred autoclave to 150° C. for 30 hours. After the mixture has cooled, petroleum ether is added and the solution is filtered off from undissolved substances and concentrated under reduced pressure. A conversion of 92% of theory is found by gas-chromatographic analysis of the residue. Subsequent distillation gives 9.9 parts of 2-nitrophenyltrimethylsilane of boiling point 116°–118° C./10 mm, corresponding to a yield of 82% of theory.

EXAMPLE 2

11 parts of 3-chloro-4-fluoronitrobenzene, 35 parts of xylene, 1.15 parts of dibenzalacetone-palladium and 0.8 part of tri-n-butylphosphine are stirred at 22° C. for 30 minutes, under nitrogen. After 10 parts of hexamethyldisilane have been added, the mixture is heated in a stirred autoclave to 150° C. for 40 hours. The mixture is allowed to cool, petroleum ether is added, and the solution is filtered off from undissolved substances and concentrated under reduced pressure. A conversion of 93% is found by gas chromatography of the residue. Distillation gives 10.8 parts of 2-fluoro-5-nitrophenyltrimethylsilane of boiling point 58°–60° C./0.1 mm, corresponding to a yield of 79% of theory.

EXAMPLES 3 TO 16

Further results of the novel process, which are obtained according to Example 1, are summarized in Table I.

TABLE I

| Compound II | Compound IV and catalyst (dba = dibenzal acetone) | Yield (% of theory) | Compound I | Physical data |
|---|---|---|---|---|
| 2-Cl-nitrobenzene | Pd(dba)$_2$ + 2.0 P(C$_6$H$_5$)$_3$ | 92 | 2-Si(CH$_3$)$_3$-nitrobenzene | b.p. 116–118° C./10mbar |
| 2-Cl-nitrobenzene | Pd(dba)$_2$ + 3.6 P(C$_6$H$_5$)$_3$ | 91 | 2-Si(CN$_3$)$_3$-nitrobenzene | b.p. 116–118° C./10mbar |
| 3-Cl-nitrobenzene | Pd(bda)$_2$ + 3.1 P(C$_6$H$_5$)$_3$ | 95 | 3-(CH$_3$)$_3$Si-nitrobenzene | b.p. 126–127/10mbar |
| 3-Cl-nitrobenzene | Pd(dba)$_2$ | 0 | — | — |
| 4-Cl-nitrobenzene | Pd(dba)$_2$ + 3.6 P(C$_6$H$_5$)$_3$ | 95 | 4-(CH$_3$)$_3$Si-nitrobenzene | m.p. 39–41° C. |
| 4-Cl-nitrobenzene | Pd(dba)$_2$ + 2.0 P(C$_6$H$_5$)$_3$ | 94 | 4-(CH$_3$)$_3$Si-nitrobenzene | m.p. 39–41° C. |
| 2-F-5-Cl-nitrobenzene | Pd(dba)$_2$ + 2.0 P(C$_6$H$_5$)$_3$ | 93 | 2-F-5-(CH$_3$)$_3$i-nitrobenzene | b.p. 58–60° C./0.1mbar |
| 2-F-5-Cl-nitrobenzene | Pd(dba)$_2$ + 3.1 P(C$_6$H$_5$)$_3$ | 91 | 2-F-5-(CH$_3$)$_3$Si-nitrobenzene | b.p. 58–60° C./0.1mbar |
| 2-F-5-Cl-nitrobenzene | Pd(dba)$_2$ + 2.0 (n-C$_4$H$_9$)$_3$P | 92 | 2-F-5-(CH$_3$)$_3$Si-nitrobenzene | b.p. 58–60° C./0,1mbar |
| 4-Cl-acetophenone | Pd(dba)$_2$ + 2.0 (C$_6$H$_5$)$_3$P | 60 | 4-(CH$_3$)$_3$Si-acetophenone | b.p. 141–143° C./20mbar |

TABLE I-continued

| Compound II | Compound IV and catalyst (dba = dibenzal acetone) | Yield (% of theory) | Compound I | Physical data |
|---|---|---|---|---|
| 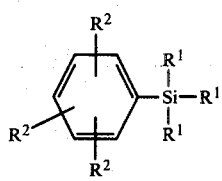 | Pd(dba)₂ + 2.0 (C₆H₅)₃P | 90 | 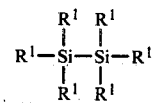 | b.p. 133-135° C./20mbar |
| 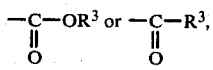 | Pd(dba)₂ + 2.0 (C₆H₅)₃P | 65 | | b.p. 118-120° C./29mbar |
| 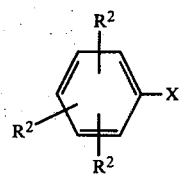 | Pd(dba)₂ + 2.0 (C₆H₅)₃P | 40 | | $n_D^{20} = 1.5113$ |

We claim:

1. A process for the preparation of aromatic silanes of the formula:

I where the individual radicals R¹ and R² can be identical or different and each is an aliphatic, cycloaliphatic, araliphatic or aromatic radical, and each radical R² can also be hydrogen, halogen, nitro, cyano, —O—R³, —C—OR³ or —C—R³,
‖           ‖
O           O where R³ is an aliphatic, cycloaliphatic, araliphatic or aromatic radical, wherein an aromatic halogen compound of the formula:

II where R² has the above meaning and X is halogen, is reacted with a disilane of the formula:

III where R¹ has the above meaning, in the presence of a palladium complex with a ketone and/or an anhydride, and in the presence of a phosphine or phosphite which is trisubstituted by aliphatic or aromatic radicals.

2. A process as claimed in claim 1, wherein the reaction is carried out using from 0.5 to 2.0 moles of starting material III per mole of starting material II.

3. A process as claimed in claim 1, wherein the reaction is carried out at from 50° to 250° C.

4. A process as claimed in claim 1, wherein the reaction is carried out from 100° to 200° C.

5. A process as claimed in claim 1, wherein the reaction is carried out using a solvent which is inert under the reaction conditions.

6. A process as claimed in claim 1, wherein the reaction is carried out using a ketone or an anhydride which has two or more carbonyl groups, triple bonds and/or double bonds.

7. A process as claimed in claim 1, wherein the reaction is carried out using from 0.001 to 0.2 gram atom of palladium per mole of starting material II.

8. A process as claimed in claim 1, wherein the reaction is carried out using from 0.5 to 5.0 moles of ketone or anhydride ligand per gram atom of palladium.

9. A process as claimed in claim 1, wherein the reaction is carried out using, as the additional catalyst, from 0.0001 to 0.8 mole of a phosphine or phosphite per mole of starting material II.

* * * * *

UNITED STATES PATENT AND TRADEMARK OFFICE
CERTIFICATE OF CORRECTION

PATENT NO.   : 4,363,925
DATED        : December 14, 1982
INVENTOR(S)  : Rolf-Dieter Acker, et al It is certified that error appears in the above-identified patent and that said Letters Patent is hereby corrected as shown below:

On the title page add:
[30] Foreign Application Priority Data
-- February 7, 1981 [DE] Federal Republic of
    Germany  .............3104326 --.

Signed and Sealed this

Seventeenth Day of May 1983

[SEAL]

Attest:

DONALD J. QUIGG

Attesting Officer   Acting Commissioner of Patents and Trademarks